United States Patent [19]

Willoughby

[11] Patent Number: 4,798,587
[45] Date of Patent: Jan. 17, 1989

[54] DEVICE FOR REMOVING NEEDLES OR NEEDLE/SHEATH COMBINATIONS FROM HYPODERMIC SYRINGES

[76] Inventor: Graham M. Willoughby, 20 Ruskin Row, Winnipeg, Manitoba R3M 2R7, Canada

[21] Appl. No.: 124,575

[22] Filed: Nov. 24, 1987

[30] Foreign Application Priority Data

Sep. 18, 1987 [CA] Canada .................................. 547225

[51] Int. Cl.$^4$ .............................................. B65F 1/16
[52] U.S. Cl. ................................................... 604/110
[58] Field of Search ........................ 604/110, 192, 263

[56] References Cited

FOREIGN PATENT DOCUMENTS 1184547 3/1985 Canada .
2601512 3/1977 Fed. Rep. of Germany ...... 604/110

Primary Examiner—Allen M. Ostrager

[57] ABSTRACT

A device for removing needles or needle/sheath combinations from hypodermic syringes. The device comprises a gripping mechanism for releasably gripping the needle or needle/sheath combination when inserted into the device. The device also includes a drive mechanism associated with the gripping mechanism for causing the gripped needle or needle/sheath combination to rotate relative to the syringe. The gripping mechanism is designed so that the needle or needle and sheath combination move freely away from the gripping mechanism when released. The rotation enables the needle or needle sheath combination to be removed from the syringe simply by moving the syringe away from the device as the rotation takes place. When released by the gripping mechanism the needle or needle/sheath combination preferably falls into a removable container within the device.

18 Claims, 2 Drawing Sheets

DEVICE FOR REMOVING NEEDLES OR NEEDLE/SHEATH COMBINATIONS FROM HYPODERMIC SYRINGES

BACKGROUND OF THE INVENTION

1. Field of the Invention

This invention relates to devices used for removing needles and needle/sheath combinations from hypodermic syringes and, preferably, for safely disposing of said needles or needle/sheath combinations.

2. Discussion of the Prior Art

Hypodermic needles can act as serious sources of infection if proper care is not taken during their removal from syringes and during their disposal. Needles are often difficult to remove from syringes after use and there is always a danger that health field workers (doctors, dentists, assistants, nurses, etc.) may accidentally puncture their hands, which significantly increase the risk of infection.

The risk of accidental puncture has been reduced (but not completely eliminated) by the common practice of providing a safety sheath or cap which envelopes the needle at all times except when the sheath is removed so that an injection may be given. Once the sheath has been re-positioned after use, the risk of accidental puncture is much reduced, but the user may still be exposed to contaminated fluids when the needle/sheath combination is removed from the syringe. For example, the inner end of the needle, i.e. the part that connects to the syringe, is not covered by the sheath and in many cases has a sharp needle-like projection for extending into the dose chamber of a syringe. The exposed inner end may be contaminated with a patient's fluids because of the tendency of fluids within the needle to flow backwards to the inner end due to the suction generated as the needle is removed from the syringe.

Devices for removing needles and needle/sheath combinations from syringes are already known. For example, Canadian Pat. No. 1,184,547 issued on Mar. 26, 1985 to Frontier Plastics (South Wales) Limited discloses a device in the form of a closed container having a keyhole shaped slot in its top wall. The slot accepts standard sized hypodermic needles and, by drawing the needles into the narrow part of the slot and pulling back on the syringe, the needles are detached and fall into the body of the container. However, needles often do not detach easily from syringes and must often be twisted or rotated relative to the syringe barrel. This is of course essential if the syringe is of the type which has a screw-threaded hollow projection onto which the removable needles are screwed. The device mentioned above does not facilitate this action (the needle may rotate in the slot and a free hand must be used to hold the container) and the needles, once removed from the syringe barrel, may be jammed in the slot and have to be freed by hand. All of this increases the risk of contamination and reduces ease of use.

Throw-away removal devices are also known, e.g. the device disclosed in U.S. Pat. No. 4,610,667 issued on Sept. 9, 1986 to Pedicano et al. This is a funnel shaped device having a closable cap for the enlarged end. The syringe and needle is inserted through the enlarged end into the narrow section where the needle is gripped using one hand and removed as the syringe is twisted and pulled back with the other. The needle remains in the device and the cap can be closed and the whole unit thrown away. Such devices are however bulky to store and expensive to use because each device is good for only one use.

Other disposable devices are shown in U.S. Pat. Nos. 4,430,082 issued to Schwabacher on Feb. 7, 1984 and 4,559,042 issued to Votel on Dec. 17, 1985, but these devices allow the user to contact the inner end of the needle as it is removed from the syringe.

Accordingly, there is a need for an improved device for removing needles or needle/sheath combinations from hypodermic syringes.

SUMMARY OF THE INVENTION

An object of the invention is to provide a device capable of removing a needle or needle/sheath combination from a hypodermic syringe without the user contacting the needle or needle/sheath combination.

The present invention provides such a device, which comprises releasable gripping means for the needle or needle and sheath combination attached to a syringe held by the user, and drive means associated with the gripping means for rotating the needle or needle and sheath combination, the releasable gripping means being designed so that the needle or needle and sheath combination may move freely away from the gripping means when released, e.g. under the action of gravity.

The releasable gripping means and the drive means are preferably located in an enclosed body having an aperture for insertion of the needle or needle and sheath combination, with the releasable gripping means being located immediately behind the aperture. The gripping means are preferably designed so that the needle or needle and sheath combination may pass completely through the gripping means, i.e. between the elements forming the gripping means, when removed from the syringe and released by the gripping means. The device may then include a removable container located in the body, for catching the needle or needle and sheath combination when released by the gripping means.

The drive means may be motor driven or alternatively may be manually operable.

DETAILED DESCRIPTION OF THE PREFERRED EMBODIMENTS

Figure 1:
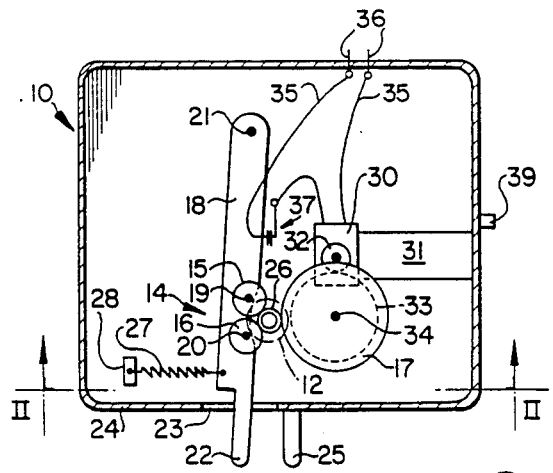
FIG. 1 is a cross-sectional view of a first preferred embodiment of the invention taken on the line I—I of FIG. 2.
Figure 2:
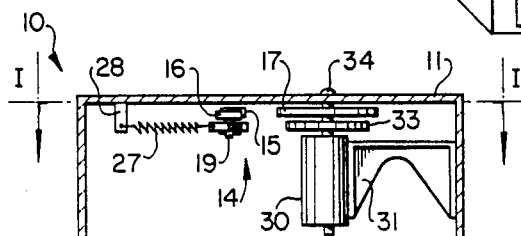
FIG. 2 is a cross-section of the device of FIG. 1 taken on the line II—II of FIG. 1.

A first embodiment of the present invention is shown in FIGS. 1 and 2. The needle or needle/sheath removal device is indicated generally by the numeral 10. The device is basically a rectangular container having side walls and a top wall 11. The top wall is provided with a circular aperture 12 (indicated in dash-dot lines in FIG. 1) having a diameter larger than the largest part of a needle or needle/sheath combination likely to be encountered, thus ensuring that the needle or needle/sheath combination can pass completely through the aperture (when removed from a syringe) into the interior of the container. The aperture should preferably not be so large, however, that the barrel of a hypodermic syringe may be inserted into the device.

A releasable gripping means 14 for the needle or needle/sheath combination is located within the device immediately below the top wall 11 in alignment with the aperture 12. The releasable gripping means comprises three rotatable wheels, i.e. a pair of small wheels 15, 16 and a large wheel 17. The pair of small wheels 15, 16 is mounted on an elongated arm 18 via pivot pins 19, 20 (respectively) and the arm 18 itself is pivotally mounted on the underside of top wall 11 via pivot pin 21 (shown in FIG. 1 but omitted from FIG. 2 for the sake of simplicity). The elongated arm 18 has a free end 22 extending outside the device through a narrow horizontal slot 23 in sidewall 24 of the device immediately below the top wall 11. A similarly-shaped projection 25 is fixed to sidewall 24 adjacent to slot 23 so that the user may squeeze the free end 23 and projection 25 together between finger and thumb. When this is done, the elongated arm 18 pivots about pin 21 and the small pair of wheels 15, 16 moves towards the large wheel 17 and, in combination, the wheels 15, 16, 17 grip any item, such as needle/sheath combination 26 (FIG. 1), projecting through aperture 12. Coil spring 27 is attached at one end to arm 18 and at the other end to fixed post 28 so that the spring urges the arm 18 to the released position.

Drive means are provided to cause rotation of the gripped item. The drive means comprises an electric motor 30 firmly anchored inside the device by bracket 31. A driven gear wheel 32 projects from the top of the motor and meshes with a larger gear wheel 33 mounted on shaft 34 which also supports wheel 17 from the top wall 11. Both wheel 17 and sprocket wheel 33 are keyed to shaft 17 so that the rotation of the small gear wheel 32 causes rotation of wheel 17 via the large gear wheel 33. The motor 30 may be operated by batteries (not shown) located in the device but is preferably connected to an external power source (not shown) via leads 35 and connectors 36. One of the leads incorporates an on/off switch 37, one terminal of which is fixed to the underside of the top wall 11 and the other terminal of which is fixed to pivotable arm 18. Movement of the free end 22 of the arm 18 towards the projection 25 causes the switch to close and consequently the motor to operate. When the spring 27 returns arm 18 to the released position, the switch 37 opens and the motor stops.

The wheels 15, 16, 17 are preferably made of rubber or other elastomeric material so that they securely grip a needle or needle/sheath combination placed between them when the free end 22 and projection 25 are squeezed together. The rotation of wheel 17 causes this needle or needle/sheath to rotate. Since wheels 15, 16 are idle (i.e. free to rotate), the rotation of the needle or needle/sheath is passed on to these small wheels which consequently retain their firm grip on the needle or needle/sheath combination while permitting the desired rotation. The device incorporates a drawer-like container 38 in its lower part beneath the hole 12. The container catches items, such as needle/sheath combination 26, which fall through the aperture 12 when released by the gripping means 14. The container has a handle 39 on its outside wall so that it may be easily withdrawn from the device when full. The container 38 may simply be emptied and then re-positioned in the device but, more preferably, the container is disposable and is replaced by a new, unused container. Although not shown, the container may have a lid for sealing the top opening and desirably the lid is difficult or impossible to remove once it has been affixed to the container. This reduces the risk of contamination from the container contents subsequent to the removal of the container from the device.

The device is normally used as follows. A hypodermic syringe having an attached needle or needle/sheath combination is held by the barrel and the needle or needle/sheath is partially or completely inserted into the hole 12. Using a free hand, the user then squeezes end 22 and projection 25 together to cause wheels 15, 16, 17 to grip the needle or needle/sheath and to cause the motor 30 to start operating. The wheels cause the needle or needle/sheath to rotate relative to the syringe (which is still held by the user) and this rotation eventually makes it possible to move the syringe away from the device while leaving the needle or needle/sheath in the device. If the needle or needle/sheath does not initially rotate, the user can squeeze end 22 and projection 25 together more tightly so that wheels 15, 16, 17 grip the needle or needle/sheath more firmly. Once the needle or needle/sheath has been detached from the syringe, the free end 22 and projection 25 are released and the spring 27 causes arm 18 to pivot away from wheel 17. This releases the needle or needle/sheath which is then free to pass completely through the hole 12 and gripping means 14 and to fall into container 38 because there is then no obstruction between the aperture 12 and the container 38 when the arm 18 has pivoted to the released position.

The device enables the user to remove a needle or needle/sheath from a syringe in a reliable and easy manner without ever touching any part of the needle or needle/sheath. Since the hole 12 is located a safe distance from free end 22 and projection 25, the user is unlikely to puncture his/her free hand when inserting a needle into hole 12.

To prevent accidental damage, at least the top wall 11 of the device should be thick or strong enough to resist puncture by a hypodermic needle.

Figure 3:
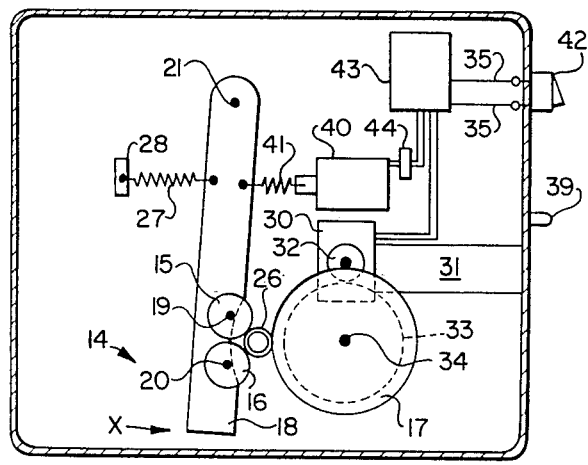
FIG. 3 is a cross-sectional view similar to FIG. 1 of a second preferred embodiment of the invention.

FIG. 3 shows a further embodiment of the invention which is similar to the previous embodiment shown in FIGS. 1 and 2 except that the gripping means are power actuated. In FIG. 3, parts of the apparatus similar to those in FIGS. 1 and 2 are identified by the same reference numerals.

In the embodiment of FIG. 3, the elongated arm 18 is moved in the direction of arrow X by means of an electrically operated solenoid 40 which is connected to arm 18 via a tight coil spring 41. The solenoid 40 is securely fixed to the underside of the tape wall (not shown) of the device. The coil spring 41 allows for some cushioning during the clamping action onto the needle or needle/sheath combination 26 and also makes it possible for the device to accommodate needles or needle/sheath combinations of different sizes. The solenoid 40 is operated by external current supplied through leads 35 and controlled by an external switch 42. However, an "interval-on" relay 43 of conventional design is located between the switch 42, the solenoid 40 and the motor 30 to ensure that the needle or needle/sheath combination remains clamped and the gripping means rotate for a minimum time sufficient for the needle or needle/sheath combination to become completely removed or unscrewed from the barrel of the syringe before the device automatically turns itself off. Additionally, a time delay relay 44 of conventional design is connected between the solenoid 40 and the interval-on relay to ensure that the large wheel 17 is rotating at proper speed before the clamping means is actuated. As in the embodiment of FIGS. 1 and 2, spring 27 (which has weaker spring force than coil spring 41) releases the clamping means 14 when the device is turned off by moving elongated arm 18 in a direction opposite to arrow X. This allows the freed needle or needle/sheath combination to drop into the container below.

Figure 4:
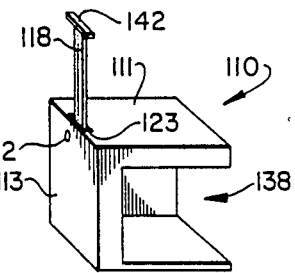
FIG. 4 is a perspective view of a device according to a third preferred embodiment of the invention.
Figure 5:
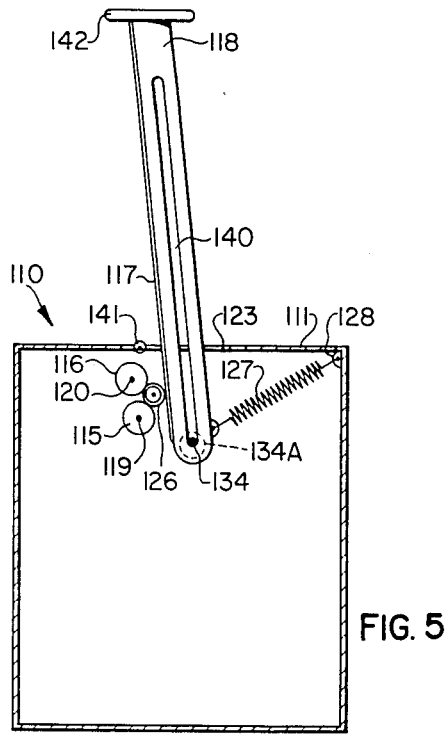
FIG. 5 is a cross-sectional view of the device of FIG. 4, the section line being immediately behind the side wall 113 of FIG. 4.

A third embodiment of the device of the invention is shown in FIGS. 4 and 5. In contrast to the previous embodiments, the drive means of this embodiment is manually operable rather than electric driven. The device is indicated generally by the reference numeral 110. The aperture 112 for the insertion of the needle or needle/sheath is in a sidewall 111 of the body adjacent to the top edge. A container (not shown) similar to the one used in the previous embodiments is slidably received in the cavity 138 provided in the body of the device below the aperture 112.

The releasable gripping means and the drive means are located in the body immediately behind the aperture 112 and are shown in detail in FIG. 5. In this embodiment, the needle or needle/sheath is gripped between a pair of small wheels 115, 116, pivotally attached to the inner surface of the sidewall 113 via pivot pins 119, 120, and an elongated rack 117 (so-called because of the "rack-and-pinion" type action employed in this embodiment, as will be apparent later) attached to a side edge of an elongated arm 118. The rack 117 has a smooth or slightly roughened flat outer surface. The arm 118 is attached to the inner surface of sidewall 113 by means of pin 134 having an enlarged head 134A at the free end of the pin. The arm has an elongated longitudinal slot 140 which allows the arm 118 to move longitudinally on the pin 134 and also to pivot on the pin 134. A coil spring 127 is attached at one and to the lower end of the arm 118 and at the other end to a tab 128 attached to the body of the device. A small roller 141 is provided on one side of a slot 123 formed in the upper wall 111 of the device. The arm 118 extends upwardly through the slot and has an enlarged end 142 set slightly obliquely relative to the longitudinal arm axis. The position of the pin 134 and the oblique arrangement of the enlarged end 142 on the arm 118 tend to make the arm pivot on the pin towards the wheels 115, 116 when it is pressed down.

The device is operated as follows. The user inserts a needle or needle/sheath combination 126 attached to a hypodermic syringe (not shown) through aperture 112 and maintains a firm grip on the barrel of the syringe. With a free hand, the user pushes arm 118 (by pressing enlarged end 142) down so that the arm pivots around pin 134 and also slides longitudinally on the pin. The rack 117 and small wheels 115, 116 grip the needle or needle/sheath between them. The wheels and rack are preferably made of rubber or other elastomeric material for a secure grip. As the arm 118 moves downwardly, the rack 117 causes the needle or needle/sheath 126 to rotate since the latter acts as a "pinion". The wheels 115, 116 are idle and are in turn caused to rotate by the motion of the needle or needle/sheath. Since the user continues to hold the syringe barrel, the rotation of the needle or needle/sheath allows the latter to be removed reliably and easily from the syringe when the syringe is moved away from the device. The arm 118 can then be pivoted away from the needle or needle/sheath 126 so that the latter is released and falls without obstruction into the container located inside the device below aperture 112. The spring 127 then returns the arm 118 to the uppermost position shown in the drawings. The roller 141 contacts the rack 117 and prevents it from becoming damaged if the arm 118 is pivoted so far over that it approaches the edge of slot 123. The length of the rack 117 is preferably such that it rotates the needle or needle/sheath up to about six times before the arm 118 is completely depressed. This number of turns should be sufficient even to deal with needles that are attached to syringes via screw threads. However, the device should of course be constructed in such a manner that the rotation unscrews the needle, rather than screws it more firmly on the syringe.

As in the previous embodiment, the device may include an emptiable and re-usable container or may include a one-use disposable container preferably having a sealing lid.

The device is preferably made of materials (e.g. metal, such as stainless steel, rubber, plastics, etc.) that can easily be sterilized.

While the embodiments described above are presently preferred, it will be apparent to persons skilled in this art that various alterations and modifications will be possible without departing from the scope of the invention as defined by the following claims. All such alterations and modifications form part of this invention.

What is claimed:

1. A device for removing a hypodermic needle or a hypodermic needle and sheath combination from a hypodermic syringe, which comprises:
   releasable gripping means for releasably gripping said needle or needle and sheath combination, said releasable gripping means being such that said needle or needle and sheath combination may move freely away from said gripping means when released; and
   drive means associated with said gripping means for rotating said needle or needle and sheath combination when gripped by said gripping means.

2. A device according to claim 1 wherein said releasable gripping means are such that said needle or needle and sheath combination may pass completely through said gripping means when released.

3. A device according to claim 1 including a container for catching said needle or needle/sheath combination when removed from said syringe and released by said gripping means.

4. A device according to claim 1 wherein said gripping means and said drive means are located inside an enclosed body and said body has an aperture adjacent to said gripping means for receiving said needle or needle and sheath combination.

5. A device according to claim 1 wherein said drive means includes a motor for operating said drive means.

6. A device according to claim 1 wherein said drive means is manually operable.

7. A device according to claim 1 wherein said gripping means comprises at least three generally co-planar circular elements capable of being moved towards or away from each other to grip or release said needle or needle and sheath combination.

8. A device according to claim 7 wherein at least two of said elements are arraged on an elongated arm which is pivoted adjacent one end and is movable by hand at an opposite end, whereby pivoting of said arm causes said at least two elements to move towards or away from at least one other circular element.

9. A device according to claim 8 wherein said drive means comprises an electric motor for rotating said at least one other circular element.

10. A device according to claim 9 including an on/off switch for said motor associated with said elongated arm such that said switch is moved to an "on" position when said arm is rotated to move said at least two elements towards said at least one other circular element.

11. A device according to claim 5 including power operated means to move said gripping means from a released position to a gripping position.

12. A device according to claim 11 including delay means to delay the operation of said power operated means for a predetermined period of time after the commencement of actuation of said motor.

13. A device according to claim 11 including timer means for ensuring that said gripping means and said motor remain in actuation for a predetermined minimum period of time.

14. A device according to claim 1 wherein said gripping means comprises a pair of rotatable, but otherwise substantially immovable, circular elements and an elongated element opposed to said circular element, said elongated element being movable longitudinally and also being tiltable towards or away from said circular elements.

15. A device according to claim 14 wherein said elongated element has a longitudinal slot and wherein a fixed pin passes through said slot to permit said longitudinal and tiltable movements.

16. A device according to claim 3 wherein said container is located in said body but is removable therefrom.

17. A device according to claim 16 wherein said container is emptiable and re-usable.

18. A device according to claim 16 wherein said container is sealable and disposable.

* * * * *